United States Patent [19]

Schneider et al.

[11] Patent Number: 4,586,987

[45] Date of Patent: May 6, 1986

[54] OBTAINING $C_1$-$C_4$-ALKYL PENTENOATES BY DISTILLATION

[75] Inventors: Heinz-Walter Schneider, Ludwigshafen; Rudolf Kummer, Frankenthal; Otto Leman, Weisenheim; Paul Panitz, Worms, all of Fed. Rep. of Germany

[73] Assignee: BASF Aktiengesellschaft, Fed. Rep. of Germany

[21] Appl. No.: 721,810

[22] Filed: Apr. 10, 1985

[30] Foreign Application Priority Data

Apr. 10, 1984 [DE] Fed. Rep. of Germany ....... 3413448

[51] Int. Cl.$^4$ .................... B01D 3/34; C07C 67/54
[52] U.S. Cl. .................... 203/32; 203/73; 560/206; 560/218
[58] Field of Search .................. 560/206, 218, 204; 203/32, 73

[56] References Cited

U.S. PATENT DOCUMENTS

| | | | |
|---|---|---|---|
| 3,778,466 | 12/1973 | Matsuda | 560/206 |
| 4,169,956 | 10/1979 | Kummer et al. | 560/206 |
| 4,171,451 | 10/1979 | Kummer et al. | 560/204 |
| 4,258,203 | 3/1981 | Platz et al. | 560/204 |
| 4,310,686 | 1/1982 | Kummer et al. | 560/204 |
| 4,316,047 | 2/1982 | Kummer et al. | 560/206 |
| 4,332,966 | 6/1982 | Isogai et al. | 560/206 |
| 4,350,668 | 9/1982 | Isogai et al. | 560/206 |
| 4,360,692 | 11/1982 | Kummer et al. | 560/206 |
| 4,404,394 | 9/1983 | Isogai et al. | 560/206 |

FOREIGN PATENT DOCUMENTS

| | | | |
|---|---|---|---|
| 95431 | 11/1983 | European Pat. Off. | 560/206 |
| 1578797 | 11/1980 | United Kingdom . | |

*Primary Examiner*—Wilbur Bascomb
*Attorney, Agent, or Firm*—Keil & Weinkauf

[57] ABSTRACT

$C_1$-$C_4$-alkyl pentenoates are obtained from reaction mixtures which contain this and which are obtained by reacting butadiene, or a butadiene-containing hydrocarbon mixture, with carbon monoxide and a $C_1$-$C_4$-alkanol, in the presence of a cobalt carbonyl catalyst and a tertiary nitrogen base at elevated temperatures and under superatmospheric pressure by a process in which (a) the liquid reaction mixture freed from excess carbon monoxide is treated with hydrogen at elevated temperatures and under from 5 to 80 bar, (b) hydrocarbons are distilled off from the resulting liquid reaction mixture, (c) the $C_1$-$C_4$-alkyl pentenoate, the alkanol and the nitrogen base are then distilled off under reduced pressure, and (d) the $C_1$-$C_4$-alkyl pentenoate is obtained by fractional distillation from the distillate containing this compound, the alkanol and the tertiary nitrogen base.

4 Claims, No Drawings

OBTAINING $C_1$–$C_4$-ALKYL PENTENOATES BY DISTILLATION

The present invention relates to a process for obtaining $C_1$–$C_4$-alkyl pentenoates, by distillation, from reaction mixtures which contain these and which are obtained by reacting butadiene, or a butadiene-containing hydrocarbon mixture, with carbon monoxide and a $C_1$–$C_4$-alkanol in the presence of a cobalt carbonyl catalyst and a tertiary nitrogen base at elevated temperatures and under superatmospheric pressure.

The preparation of pentenoates by reacting butadiene, or a butadiene-containing hydrocarbon mixture, with carbon monoxide and an alkanol in the presence of a cobalt carbonyl catalyst and a tertiary nitrogen base has been disclosed in British Pat. No. 1,578,797. The alkyl pentenoates are isolated from the reaction mixture by distillation. However, we have found that, during the distillation, part of the catalyst decomposes while another part passes over together with the alkyl pentenoates and contaminates these. This necessitates expensive industrial purification operations and furthermore results in deposits in the apparatuses.

It is an object of the present invention to isolate $C_1$–$C_4$-alkyl pentenoates from reaction mixtures containing these by a method in which the $C_1$–$C_4$-alkyl pentenoates obtained are not contaminated by cobalt carbonyl catalysts, and the said catalysts do not decompose during the distillation and are obtained in a reusable form.

We have found that this object is achieved by a process for obtaining $C_1$–$C_4$-alkyl pentenoates, by distillation, from a reaction mixture which contains these and which is obtained by reacting butadiene, or a butadiene-containing hydrocarbon mixture, with carbon monoxide and a $C_1$–$C_4$-alkanol in the presence of a cobalt carbonyl catalyst and a tertiary nitrogen base at elevated temperatures and under superatmospheric pressure, wherein
  (a) the liquid reaction mixture freed from excess carbon monoxide is treated with hydrogen at elevated temperatures and under from 5 to 80 bar,
  (b) hydrocarbons are distilled off from the resulting liquid reaction mixture,
  (c) the $C_1$–$C_4$-alkyl pentenoate, the alkanol and the tertiary nitrogen base are then distilled off under reduced pressure, and
  (d) the $C_1$–$C_4$-alkyl pentenoate is obtained by fractional distillation from the distillate containing this compound, the alkanol and the tertiary nitrogen base.

The novel process has the advantages that $C_1$–$C_4$-alkyl pentenoates are obtained free from cobalt carbonyl compounds, decomposition of cobalt carbonyl catalysts is avoided, and the said catalysts are obtained in a reusable, active form.

In the preparation of $C_1$–$C_4$-alkyl pentenoates, pure buta-1,3-diene or a butadiene-containing hydrocarbon mixture is used as a starting material. In addition to containing butadiene, such hydrocarbon mixtures contain, for example, saturated hydrocarbons of 3 to 5 carbon atoms and monoolefinicaLLy unsaturated hydrocarbons of 3 to 5 carbon atoms. As a rule, the butadiene content should be more than 10% by weight. In industry, in particular, $C_4$ cuts are used as starting mixtures. All mixtures of predominantly straight-chain $C_4$-hydrocarbons which contain more than 10% by weight of buta-1,3-diene are defined as such. Typical mixtures contain from 40 to 60% by weight of butadiene, from 20 to 35% by weight of isobutene, from 10 to 25% by weight of but-1-ene, from 5 to 15% by weight of but-2-ene and from 1 to 10% by weight of butanes. Such $C_4$ cuts are obtained, for example, in the dehydrogenation of butane or butene, and as by-products in the production of ethylene by thermal cracking of light gasoline or higher hydrocarbon cuts.

The reaction is carried out using a $C_1$–$C_4$-alkanol, in particular methanol, in excess, for example from 1.5 to 5 moles of $C_1$–$C_4$-alkanol per mole of butadiene.

The reaction is effected at elevated temperatures and under superatmospheric pressure, preferably at from 80° to 150° C., in particular from 120° to 140° C., and under from 300 to 1,200, in particular from 600 to 1,200, bar. Carbon monoxide is advantageously used in excess, e.g. from 1.5 to 10 times the stoichiometric amount.

The cobalt catalyst used is advantageously introduced into the mixture in the form of cobalt carbonyl, in particular in solution in butadiene or the $C_4$ cut. Particularly advantageously, the cobalt carbonyl catalyst recovered in the reaction is used. It has proven useful to employ from 0.05 to 0.15 g atom of cobalt, in the form of cobalt carbonyl, per mole of butadiene.

The tertiary nitrogen base present advantageously has a $pK_a$ of from 3 to 11. N-heterocyclic compounds, such as pyridine, methylpyridines, such as 3-picoline, isoquinoline or quinoline, or mixtures of these are preferably used. Pyridine has become particularly important industrially. Advantageously, from 0.5 to 1.5, in particular from 0.8 to 1.2, moles of a tertiary nitrogen base are used per mole of butadiene.

When the reaction is complete, the excess carbon monoxide is separated off from the liquid reaction mixture by letting down the pressure. In addition to containing unreacted butadiene, the liquid reaction mixture thus obtained may contain hydrocarbons, the tertiary nitrogen base, the cobalt carbonyl catalyst, excess alkanol, the alkyl pentenoate produced as the end product, and by-products, such as valerates, butyl ketones and butadiene polymers. Suitable mixtures are obtained by, for example, the process described in British Pat. No. 1,578,797.

The liquid reaction mixture is treated with hydrogen at elevated temperatures, preferably from 80° to 130° C., in particular from 100° to 120° C., under from 5 to 80, advantageously from 10 to 50, bar, advantageously for from 1 to 60 minutes.

The hydrocarbons present in the resulting liquid reaction mixture are distilled off from this mixture, advantageously after removing the hydrogen. Thereafter, the $C_1$–$C_4$-alkyl pentenoate, the alkanol, the nitrogen base and, where relevant, by-products are distilled off under reduced pressure, e.g. from 1 to 200 mbar. Advantageously, the bottom temperature is kept at <80° C., in particular from 40° to 70° C., during the distillation. The cobalt carbonyl catalyst remaining in the bottom retains its activity and can be reused for the reaction.

The $C_1$–$C_4$-alkyl pentenoate is obtained by fractional distillation from the distillate which contains this compound, the alkanol and the tertiary nitrogen base and may contain by-products.

$C_1$–$C_4$-alkyl pentenoates obtainable by the invention are useful for the preparation of adipates or of alkyl δ-formylvalerates, an intermediate for the preparation of caprolactam.

The Example which follows illustrates the process according to the invention.

EXAMPLE

A high pressure vessel having a capacity of 2 is charged with 450 ml/hour of a $C_4$ cut, containing 40% by weight (2 moles) of butadiene and 0.8 g of cobalt as cobalt hydrogen carbonyl, 100 ml/hour (2 moles) of pyridine, 96 ml/hour (2.4 moles) of methanol and 32 ml/hour of a catalyst solution, containing 2.4 g of cobalt carbonyl, as a bottom product of the distillation. At the same time, 160 (S.T.P.) of carbon monoxide are fed in. Carbonylation takes place at 135° C. and under 900 bar. The product removed from the high pressure vessel is let down, excess carbon monoxide being separated off. Thereafter, the reacted liquid mixture is treated continuously with hydrogen at 110° C. and under a hydrogen pressure of 30 bar, the residence time being 10 minutes. The mixture is let down, after which the unreacted $C_4$-hydrocarbons are first distilled off under atmospheric pressure and at a bottom temperature of 90° C. Methyl pentenoate, methanol, pyridine and by-products are then separated off under reduced pressure (50 mbar) at 60° C. 40 ml/hour of catalyst solution containing 3.2 g of cobalt are obtained as a bottom product in the column. A cobalt-free mixture consisting of unreacted methanol, pyridine and methyl pentenoate is taken off at the top of the column. Under the conditions set, no cobalt is found to separate out in the bottom of the column. The distillate taken off at the top of the column is separated into methanol, pyridine and methyl pentenoate, this distillation being carried out in another column and under atmospheric pressure. In this distillation, 16 ml/hour of methanol and 160 ml/hour of pyridine are removed at the top of the column and recycled to the reaction. 225 ml/hour (92% yield) of methyl pentenoate are obtained at the bottom of the column.

The bottom product of the column, which contains the cobalt carbonyl catalyst, is then usually divided. About 80% of it is recycled to the synthesis, while 20% are separated off and worked up by oxidation, the cobalt catalyst being recovered as a $Co^{2+}$ salt.

We claim:

1. A process for obtaining a $C_1$–$C_4$-alkyl pentenoate, by distillation, from a reaction mixture which contains this and which is obtained by reacting butadiene, or a butadiene-containing hydrocarbon mixture, with carbon monoxide and a $C_1$–$C_4$-alkanol in the presence of a cobalt carbonyl catalyst and a tertiary nitrogen base at elevated temperatures and under superatmospheric pressure, wherein
   (a) the liquid reaction mixture freed from excess carbon monoxide is treated with hydrogen at elevated temperatures and under from 5 to 80 bar,
   (b) hydrocarbons are distilled off from the resulting liquid reaction mixture,
   (c) the $C_1$–$C_4$-alkyl pentenoate, the alkanol and the tertiary nitrogen base are then distilled off under reduced pressure, and
   (d) the $C_1$–$C_4$-alkyl pentenoate is obtained by fractional distillation from the distillate containing this compound, the alkanol and the tertiary nitrogen base.

2. A process as claimed in claim 1, wherein the treatment with hydrogen is carried out at from 80° to 130° C.

3. A process as claimed in claim 1, wherein the treatment with hydrogen is carried out under from 10 to 50 bar.

4. A process as claimed in claim 1, wherein the $C_1$–$C_4$-alkyl pentenoate, the alkanol and the tertiary nitrogen base are distilled off at below 80° C. from the reaction mixture containing the cobalt carbonyl catalyst.

* * * * *